(12) United States Patent
Landon

(10) Patent No.: US 11,759,325 B2
(45) Date of Patent: Sep. 19, 2023

(54) INSTRUMENTS FOR KNEE PLACEMENT

(71) Applicant: Smith & Nephew, Inc., Memphis, TN (US)

(72) Inventor: Ryan Lloyd Landon, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/734,001

(22) Filed: Apr. 30, 2022

(65) Prior Publication Data

US 2022/0265433 A1 Aug. 25, 2022

Related U.S. Application Data

(60) Continuation of application No. 16/944,676, filed on Jul. 31, 2020, now abandoned, which is a
(Continued)

(51) Int. Cl.
*A61B 17/15* (2006.01)
*A61B 17/17* (2006.01)
(Continued)

(52) U.S. Cl.
CPC .......... *A61F 2/3859* (2013.01); *A61B 17/154* (2013.01); *A61B 17/1659* (2013.01);
(Continued)

(58) Field of Classification Search
CPC .............. A61B 17/154; A61B 17/1675; A61B 17/1764; A61B 17/1659; A61B 17/157; A61F 2/389; A61F 2002/30884
See application file for complete search history.

(56) References Cited

U.S. PATENT DOCUMENTS 4,708,655 A 11/1987 Weissman
5,053,035 A 10/1991 McLaren
(Continued)

FOREIGN PATENT DOCUMENTS

DE 10120162 C1 7/2002
JP 200229087 A 8/2000
(Continued)

OTHER PUBLICATIONS

International Search Report; International Searching Authority; International PCT Application No. PCT/US2011/047542; dated Mar. 22, 2012; 3 pages.

*Primary Examiner* — Dinah Baria
(74) *Attorney, Agent, or Firm* — KDW Firm PLLC

(57) ABSTRACT

There are provided various embodiments of medical instruments to perform knee surgery. In one embodiment a finned platform for mounting a cutting block is provided. The finned platform can be used on either a femur or tibia to allow for the proper cuts when performing a knee surgery. In another embodiment, a tibial trial is shown having a fin. The fin is useful to reinforce the bone to reduce the risk of fracture during bone preparation. In another embodiment, a reamer is provided having a plurality of cutting flutes. It may be desirable to utilize a guide with the reamer to allow the reamer to cut a non-circular portion of the tibial bone. In yet another embodiment, a plurality of fixation pegs are provided on the tibial implant to allow for easy removal of such implant if a revision surgery becomes necessary.

16 Claims, 15 Drawing Sheets

Related U.S. Application Data continuation of application No. 15/077,055, filed on Mar. 22, 2016, now abandoned, which is a division of application No. 13/816,844, filed as application No. PCT/US2011/047542 on Aug. 12, 2011, now Pat. No. 9,301,846.

(60) Provisional application No. 61/373,709, filed on Aug. 13, 2010.

(51) Int. Cl.
  *A61F 2/38* (2006.01)
  *A61B 17/16* (2006.01)
  *A61B 17/92* (2006.01)
  *B33Y 80/00* (2015.01)
  *A61F 2/30* (2006.01)
  *A61B 17/90* (2006.01)

(52) U.S. Cl.
  CPC .......... *A61B 17/1675* (2013.01); *A61B 17/92* (2013.01); *A61F 2/389* (2013.01); *A61F 2/3877* (2013.01); *A61B 17/155* (2013.01); *A61B 17/157* (2013.01); *A61B 17/1764* (2013.01); *A61B 17/90* (2021.08); *A61B 2017/922* (2013.01); *A61F 2002/30332* (2013.01); *A61F 2002/30354* (2013.01); *A61F 2002/30405* (2013.01); *A61F 2002/30604* (2013.01); *A61F 2002/30884* (2013.01); *A61F 2210/0004* (2013.01); *A61F 2310/00011* (2013.01); *B33Y 80/00* (2014.12)

(56) References Cited

U.S. PATENT DOCUMENTS

| | | | |
|---|---|---|---|
| 5,129,909 | A | 7/1992 | Sutherland |
| 5,246,441 | A | 9/1993 | Ross et al. |
| 5,486,180 | A | 1/1996 | Dietz et al. |
| 5,514,139 | A | 5/1996 | Goldstein et al. |
| 5,817,097 | A | 10/1998 | Howard et al. |
| 6,620,168 | B1 | 9/2003 | Lombardo et al. |
| 7,806,898 | B2 | 10/2010 | Justin et al. |
| 7,942,879 | B2 | 5/2011 | Christie et al. |
| 8,523,869 | B2 | 9/2013 | Seifert et al. |
| 2006/0106393 | A1 | 5/2006 | Huebner et al. |
| 2006/0229726 | A1 | 10/2006 | Ek |
| 2006/0276796 | A1 | 12/2006 | Creger et al. |
| 2009/0287214 | A1 | 11/2009 | Yu |
| 2010/0063507 | A1 | 3/2010 | Sidebotham et al. |
| 2011/0015634 | A1 | 1/2011 | Smith et al. |
| 2011/0213426 | A1 | 9/2011 | Yedlicka et al. |
| 2011/0245876 | A1 | 10/2011 | Brumfield |
| 2011/0270326 | A1 | 11/2011 | Black et al. |

FOREIGN PATENT DOCUMENTS

| | | |
|---|---|---|
| WO | 20060127486 A2 | 11/2006 |
| WO | 2007057680 A2 | 5/2007 |

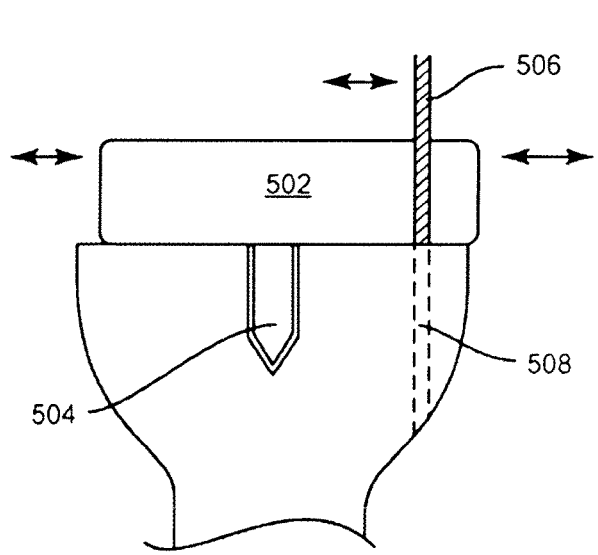
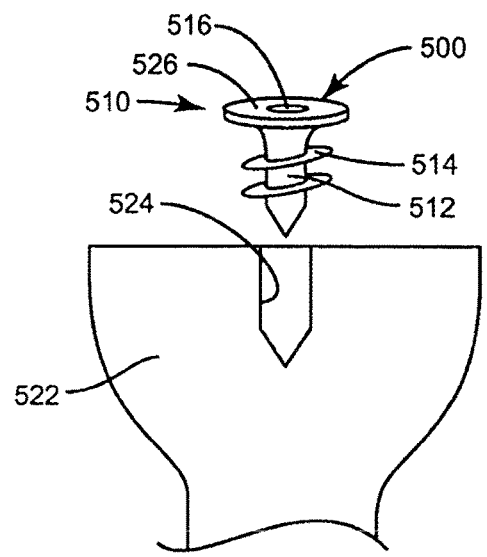
FIG. 15
(PRIOR ART)
FIG. 16
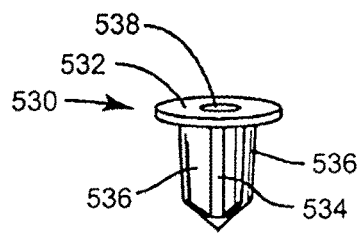
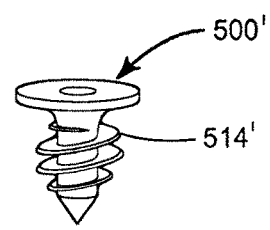
FIG. 16A
FIG. 16B
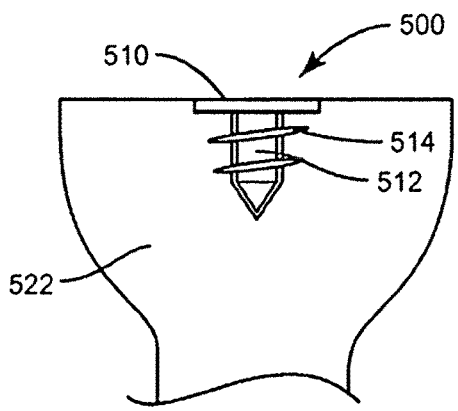
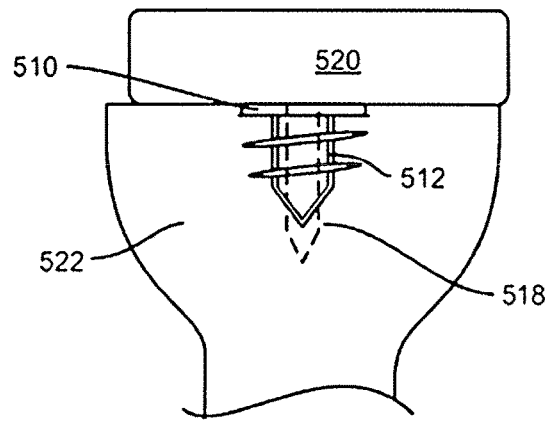
FIG. 17
FIG. 18

INSTRUMENTS FOR KNEE PLACEMENT

CROSS-REFERENCE TO RELATED APPLICATIONS

The present application is a continuation of pending U.S. patent application Ser. No. 16/944,676 filed on Jul. 31, 2020, which is a continuation of U.S. patent application Ser. No. 15/077,055 filed on Mar. 22, 2016, now abandoned, which is a divisional of U.S. patent application Ser. No. 13/816,844 filed on Mar. 12, 2013, now U.S. Pat. No. 9,301,846, which is a U.S. National Phase of International PCT Application No. PCT/US2011/047542 filed on Aug. 12, 2011, which claims the benefit of U.S. Provisional Patent Application Ser. No. 61/373,709 filed on Aug. 13, 2010. The contents of each application are incorporated by reference in their entirety.

RELATED FIELDS

Orthopaedic implants and methods involving the same, such as, but not limited to, orthopaedic implants and methods for the proximal tibia, such as tibial trays that may include one or more of a keel and/or a stem and methods for revising the same.

BACKGROUND OF THE INVENTION

There are several factors that are potentially relevant to the design and performance of orthopaedic implants. In the example of a tibial tray, a non-exhaustive list of such factors includes the implant's flexibility (or the flexibility of certain portions of the implant or its flexibility about certain axes or other constructs), which may indicate the degree to which the tray will conform to the potentially uneven resected surfaces of a proximal tibia; the implant's rigidity (or the rigidity of certain portions of the implant or its rigidity about certain axes or other constructs), which may indicate the degree to which stresses or other forces imposed by the bony and other anatomy associated with the knee joint will be transmitted to the peripheral hard cortical shell of the proximal tibia; the implant's resistance to rotation; the amount of bone preserved; and/or other potentially relevant factors. In some instances, accommodation of these or other factors may require trade-offs to balance competing factors. In some instances, one or more of these factors will not be considered or given a high level of importance to the design of an orthopaedic implant.

Some known tibial trays include a fin or a keel that may increase the strength of the implant while also helping to prevent rotation relative to the bone. In some instances, such fins or keels may present certain drawbacks. For instance, in some cases, the fin or keel may impede the visualization of the implant and surrounding anatomy using x-ray or other imaging technologies. For instance, it may be desirable in some cases to visualize the implant and its surrounding anatomy, including the surrounding bony anatomy, by taking one or more x-rays in planes such as coronal and sagittal planes or in other planes to assess whether the implant may be loosening over time. Such loosening might be indicated by lucent lines appearing in the x-ray image around portions of the implant or other indications that the bone has receded from the implant or otherwise has become loose. In some instances, a fin or keel of the implant may obstruct the ability to view such lucent lines or may otherwise hinder the evaluation of the image. Other orthopaedic components might feature these or other structures similarly impairing visualization of the implant in the bone and other anatomy.

Some known tibial trays are difficult to remove or revise. For some revision procedures, it is necessary to cut around the existing implant or otherwise position instrumentation about the implant to loosen it from the surrounding bone and/or other anatomy before removal. In some instances, particularly, for instance, some instances where the implant is a tibial tray having a keel, it may be difficult to cut around certain portions of the keel or otherwise access certain areas of the bone-implant interface to loosen the implant. It may be particularly difficult, for instance, to access certain areas of the bone-implant interface depending on the surgical approach taken. For instance, if an anterior-medial incision is used to access the knee joint, the keel structure may impede a surgeon's access to posterior-lateral portions of the bone-implant interface. In such instances, removal of the implant may undesirably require excessive or unintended bone removal as well.

In some instances, stability or fixation of the implant, such as a tibial tray or other implant, in the bone may be of some significance. For instance, the distribution of "hard" versus "soft" bone is not always uniform or predictable, and, in some instances, during bone preparation a punch, drill or other instrument may penetrate the bone at an undesired angle or position since it may tend to follow the path of least resistance into softer bone. Moreover, in some instances, such as some tibial cases, distal metaphyseal bone may tend to be spongier and softer than proximal metaphyseal bone. In some implant cases, it may be difficult to achieve adequate fixation or other stability in the distal metaphyseal bone. Moreover, with some implants, including some tibial implants, there may be a tendency over time for the implant to subside or migrate.

BRIEF SUMMARY OF THE INVENTION

There are provided various embodiments of medical instruments to perform knee surgery. In one embodiment a finned platform for mounting a cutting block is provided. The finned platform can be used on either a femur or tibia to allow for the proper cuts when performing a knee surgery. In another embodiment, a tibial trial is shown having a fin. The fin is useful to reinforce the bone to reduce the risk of fracture during bone preparation. In another embodiment, a reamer is provided having a plurality of cutting flutes. It may be desirable to utilize a guide with the reamer to allow the reamer to cut a non-circular portion of the tibial bone. In yet another embodiment, a plurality of fixation pegs are provided on the tibial implant to allow for easy removal of such implant if a revision surgery becomes necessary. In yet another embodiment, various rasp type instruments are shown to properly prepare the tibia for a tibial implant. In some embodiments, the tibial trial is provided with a rasp feature to allow the trial to be used to properly prepare the tibia for the tibial implant.

Some of the non-limiting embodiments of tibial trays described herein include one or more fins or keels that include or define holes, openings, recesses, areas formed or filled with different materials, or other structures or features. Some of the non-limiting embodiments of tibial trays described herein may additionally or alternatively include a monolithic, modular or otherwise connected fluted stem. The present application is not limited to tibial trays; however, and one of skill in the art will recognize that at least some of the concepts presented herein could be applied to other orthopaedic implants.

BRIEF DESCRIPTION OF THE DRAWINGS

FIGS. 15-18 illustrate a finned platform for mounting a cutting block.

DETAILED DESCRIPTION OF THE INVENTION

Figure 1:
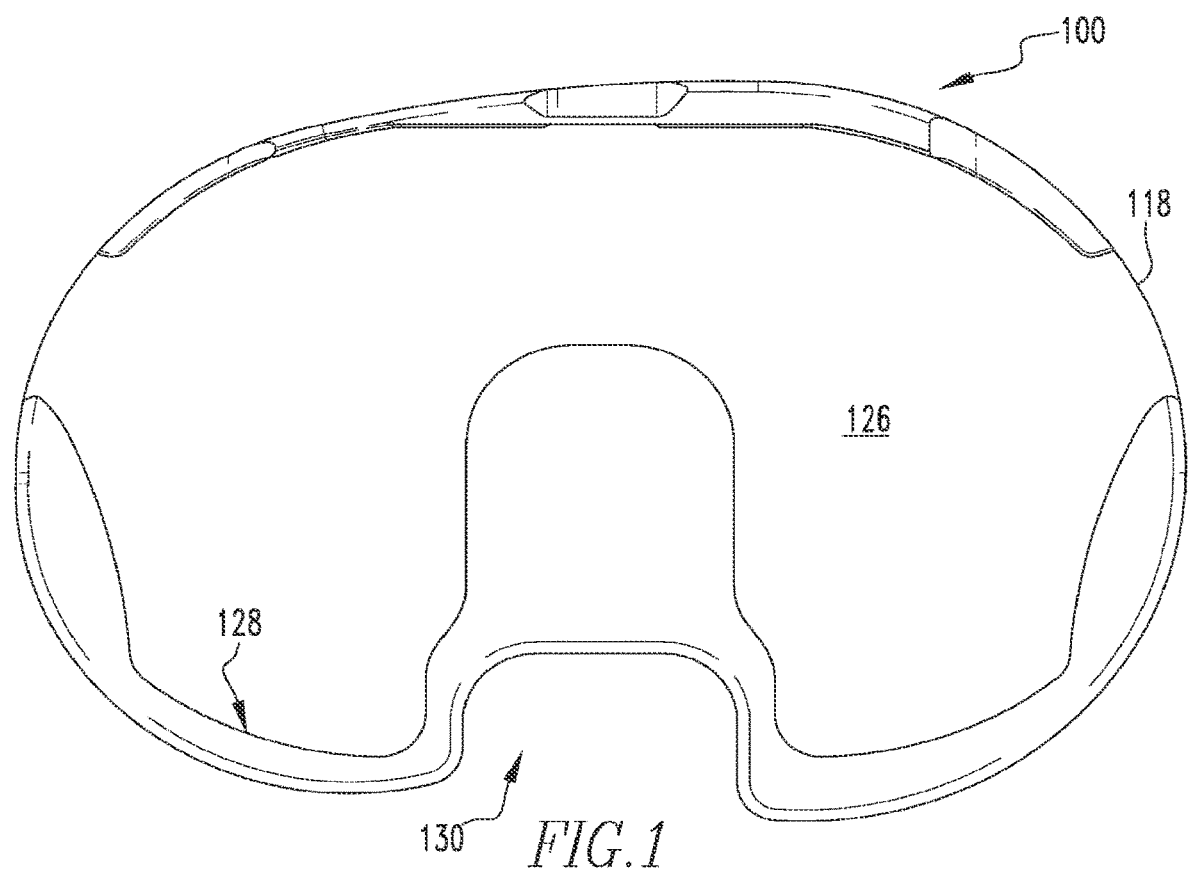
FIG. 1 is a top plan view of one non-limiting example of a tibial tray.
Figure 2:
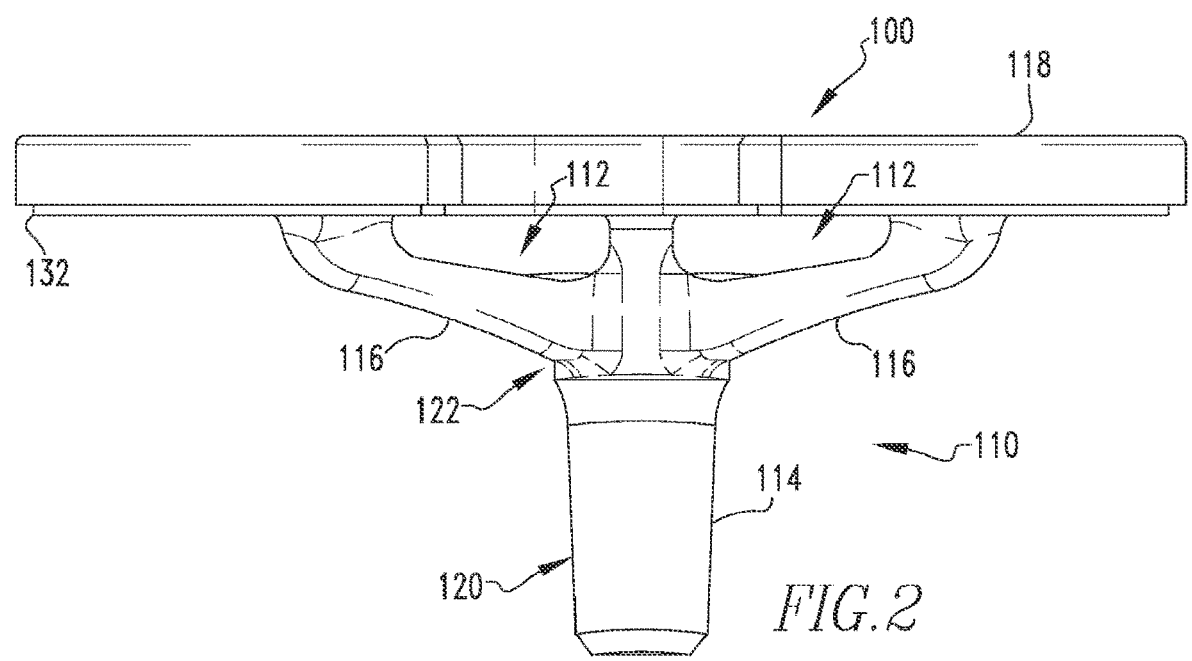
FIG. 2 is a rear elevation view of the tibial tray of FIG. 1.
Figure 3:
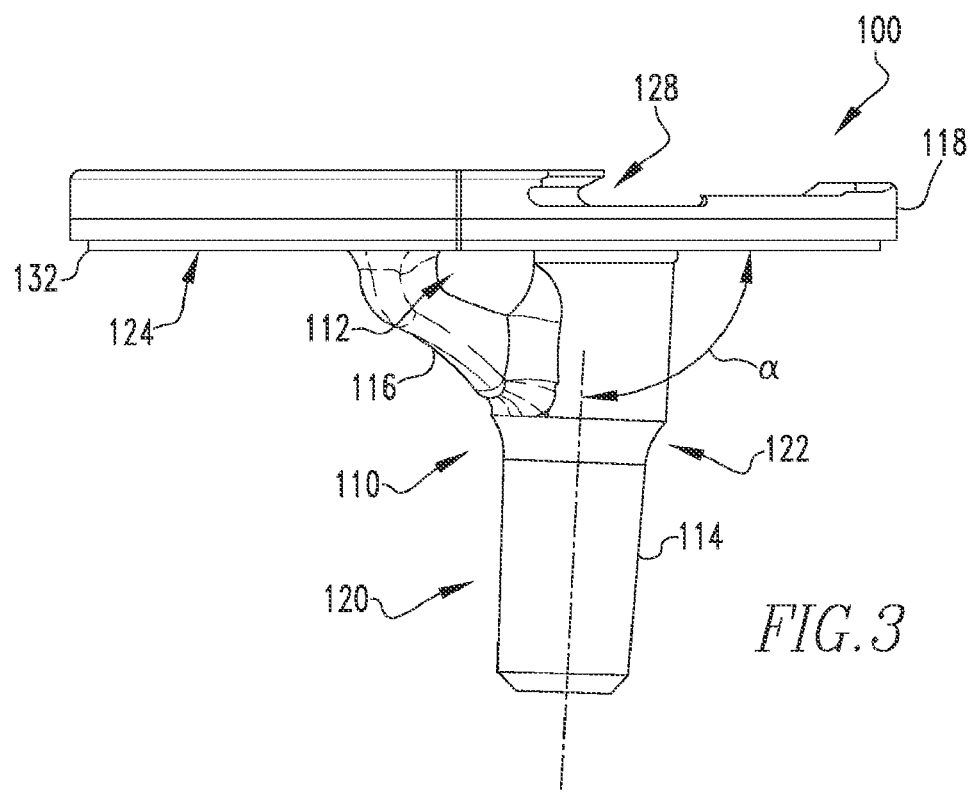
FIG. 3 is a side elevation view of the tibial tray of FIG. 1.

FIGS. 1 through 3 illustrate a non-limiting example of a tibial component 100. As shown in FIGS. 2 and 3, the tibial component 100 includes support member 110 defining a pair of openings 112. In some, although not necessarily all, embodiments, these openings may be sized, positioned, oriented and otherwise constructed to: (1) reduce by a certain degree the stiffness of the implant while maintaining a certain degree of strength; (2) facilitate the visualization (such as through x-ray imaging or other techniques) of lucent lines or other signs that the implant is loosening; (3) facilitate the loosening of the tray from the bony anatomy in the event resection is necessary, such as by facilitating the movement of cutting or other types of instrumentation through and to the far side of the keel/stem portion that would not otherwise be accessible to the cutter or other instrumentation; and/or (4) facilitate bony-ingrowth or otherwise enhance the stability of the implant in the bone. In some embodiments, the openings may not feature all of these benefits or may provide other beneficial features.

The support member 110 shown in FIGS. 2 and 3 includes a stem portion 114 and two arms 116 extending therefrom. In this particular example, the support member 110 is attached to an underside of a tibial tray 118 at three points forming a tripod-like construct. The stem portion 114 shown includes a lower cylindrical portion 120 and an upper portion 122 that is blended to the arms 116. In the depicted embodiment, the stem portion 114 slants at an angle a and in an anterior-posterior direction as it extends away from an inferior surface 124 of the tray 118; however, in other embodiments, the stem portion 114 may have other geometries. The stem portion 114 of this particular tibial component 100 is located anteriorly on the tray 118, although other locations are also possible. The arms 116 shown in FIGS. 2 and 3 extend posteriorly and outwardly from a mid-point of the stem 114 and curve to connect to the underside of the tibial tray 118. In other embodiments, other numbers of arms and/or stems in other configurations and geometries can be employed.

The arms 116 and stem portion 114 of the support member 110 shown in FIGS. 2 and 3 define two openings 112 abutting the inferior surface 124 of the tibial tray 118. In other embodiments, different numbers, configurations, shapes, orientations, and positionings of the openings may be possible. As discussed below, in some embodiments, the openings 112 of the support member 110 may not be "openings" at all in the traditional sense, but may be areas where other materials or components are located, or in which the material forming the tibial component 100 has different properties or characteristics.

In some embodiments, the openings 112 formed in the support member 110 increase certain flexibility characteristics of the tibial component 100 while not overly impinging on a desired strength characteristic of the component. In some embodiments, the openings 112 can be sized and shaped so that the remaining solid material is relatively uniform in shape. In some embodiments, the remaining solid material is uniform in shape in the regions of highest stress at the most peripheral edges of the arms 116. In some embodiments, the opening size can be configured to be short enough to allow a sawblade to easily clear material away from the sides while being tall enough to allow a thin and narrow osteotome to pass through in order to facilitate revision surgery. In other embodiments, the openings 112 may be configured to only permit a sawblade or an osteotome, but not both. In some embodiments, such as, for example, where revisability is not a primary goal, taller and deeper openings may be used to facilitate maximal ingrowth through and around the openings.

In some embodiments, the openings 112 formed in the support member 110 provide for better visualization of the tibial component 100, the bone surrounding the tibial component, and the interface or interfaces between the bone and the tibial component 100. The openings 112, in some embodiments, may act as "windows" facilitating the visualization of lucent lines or other visual indications on the imaging data, which may suggest or indicate that the tibial component is loosening or provide other information for evaluating other issues or concerns. In some embodiments, the size, shape, placement and/or orientation of the openings 112 can be optimized to facilitate visualization of bone-implant interfaces and other areas of interest for future visualization of the implant after installation. For instance, as shown in the Figures, the openings 112 are primarily oriented in a coronal plane, although, in other embodiments, they could be primarily oriented in a sagittal plane or other orientations. In some embodiments, a wider attachment region with a less abrupt thickness change may be used to provide for lower stress in the region. In some embodiments, a more narrow attachment region may be used to increase visibility by lessening the amount of material that could block a user's view.

In some embodiments, the openings 112 are not physical openings extending through the support member 110 or other portion of the tibial component, but may instead be components or areas that do not completely or partially impair visualization such as by x-ray technologies or other visualization technologies. For instance, in some embodiments, the "openings" may be filled or may be comprised of materials of lower density (such as materials for facilitating bony in-growth or other materials) or that are otherwise semi or completely radio-lucent.

In some embodiments, the openings 112 allow a cutting device or other instrument to physically pass through one or more of the openings 112 to facilitate cutting or otherwise loosening the tibial component from the bone in the event a revision procedure is necessary. In the embodiment shown in FIGS. 2 and 3, the openings 112 are oriented such that posterior-lateral portions of the bone-implant interface can be accessed by a surgical cutter or other instrument if an anterior-medial approach to accessing the joint space is used. The openings 112 shown in FIGS. 2 and 3 also may allow this and other portions of the bone-implant interface to be accessed from other approaches or directions. In other embodiments, the position, orientation, size, shape and number of openings 112 could be altered to facilitate access to remote portions of the bone-implant interface depending on the particular implant involved, the expected surgical approach or approaches that may be utilized, and/or other factors (e.g. the size and shape of the instrument(s) that might need to pass through the opening). In some embodiments, the "openings" are not necessarily physical openings through the support member 110 but are areas that are frangible or otherwise capable of being relatively-easily penetrated by a surgical instrument to access the remote portions of the bone-implant interface if necessary. In some embodiments, the opening(s) could be designed to function as guides for the instrumentation passing through them, which, in some uses, might control depth and/or direction of insertion of the instrument (e.g. to lessen chance of damaging surrounding anatomy, such as postero-lateral nerves or arteries) or other aspects of the procedure. In some embodiments, openings 112 can be configured for improved visibility and an ability to approach from anterior to posterior. In some embodiments, the opening(s) 112 could be designed to accommodate surgical cutting instruments such as reciprocating or oscillating planar saw blades having cutting edges on either or both of a distal end or one or both sides, milling bits and other types of rotating cutting devices, chisels, other osteotomes, prying devices, or any other type of surgical instrument that might be used for a revision procedure.

As mentioned above, in some embodiments, the openings 112 could be filled with a porous structure or material or otherwise define in-growth surfaces. In some embodiments, the porous structure or material could be formed from the same material as the rest of the support member 110 but having a different porosity, density or other characteristics than other portions of the support member 110. In some embodiments, the porous structure is not necessarily confined to the opening 112 and could occupy geometric volumes outside of and around other portions of the support member 110. Indeed, in some embodiments, the support member 110 could function as an internal scaffolding for a volume of bone in-growth material(s) that completely or at least in portions encompass the support member 110. In other embodiments, other materials or structures may fill the openings 112 and a porous structure or treatment is not necessary. In some embodiments, the filling material or structure may be intended to facilitate anti-rotation aspects of the implant.

FIG. 1 shows a superior surface 126 of the tibial tray 118, which includes attachment feature 128 for receiving and/or securing one or more articular inserts (not shown) to the tibial tray 118, such inserts designed to contact and articulate with a femoral orthopaedic implant (not shown) in use. In the depicted embodiment, the attachment feature 128 is a shaped channel to receive and lock-in the articular insert. In other embodiments, the tibial tray 118 itself may include articular surfaces and does not require separate articular inserts. The tibial tray 118 shown in FIGS. 1 through 3 includes a posterior notch 130, which may be designed to allow preservation of the attachment site of a posterior cruciate ligament, although, in other embodiments, the tibial tray 118 may or may not include this or other notches or gaps for preserving one or both of the cruciate ligaments. In other words, the tibial tray, in some embodiments, may be for use in a cruciate sacrificing procedure, a posterior cruciate preserving procedure, or a bi-cruciate preserving procedure. In some embodiments, the tibial tray 118 may be used for a mobile bearing knee joint or a fixed bearing knee joint. It will be appreciated that a variety of upper surface and peripheral shapes are possible according to various embodiments and that such shapes can be influenced, at least in part, by strength requirements for the tray. For example, in some embodiments, a cruciate notch or dovetail mechanism may be used, but may also act as a stress-riser.

The tibial component 100 shown in FIGS. 1 through 3 may be part of a set of tibial trays of various standard sizes, or may be a patient-matched tibial tray with certain geometries and/or other aspects of the tray customized for a particular patient's anatomy. The tibial component 100 shown in FIGS. 1 through 3 may be formed from biocompatible materials typically used to manufacture orthopaedic implants or may be formed from other materials. The tibial component 100 shown in FIGS. 1 through 3 may be formed using any desired or appropriate methodologies or technologies.

In some embodiments, the tibial component 100 may be manufactured using Selective Laser Sintered technologies ("SLS") or other free-form fabrication technologies, such as one or more of the EOS Laser-Sintering systems available from EOS GmbH of Munich, Germany. For instance, in some embodiments, the entire tibial component 100 may be formed as a monolithic implant (including any porous or other in-growth promoting surfaces or materials). In other embodiments, portions of the tibial component 100 may be formed using SLS technology and then additional in-growth materials, surfaces, and/or treatments could be added or applied to the implant. In other embodiments, electron beam melting methods or methods that use lasers to subtract or remove select portions of material from an initially solid fin may be used. In other embodiments, portions or all of the tibial component can be formed using casting or other technologies or methods. In some embodiments, a non-porous implant such as a tibial component may be formed using SLS technologies and subsequently that implant may be subjected to acid etching, grit blasting, plasma spraying (e.g. of titanium oxide or another metal to promote in-growth) or other treatments.

FIGS. 4 through 8 illustrate a modular stem 200 that may be used with the tibial component 100 of FIGS. 1 through 3 in some, although not necessarily all, embodiments. Indeed, in some embodiments, the tibial component of FIGS. 1 through 3 will be used without any modular stem or otherwise incorporating any of the features or constructs of the modular stem shown in FIGS. 4 through 8. The modular stem 200 may connect to the stem portion 114 of the support member 110 of the tibial component of FIGS. 1 through 3 via a taper fit mechanism (which may be further secured by a screw or other fastener in some embodiments). In other embodiments, other mechanical attachment mechanisms may be employed, or, in still other embodiments, the stem is not modular but an integral part of the tibial component.

The embodiment of the modular stem 200 shown in FIGS. 4 through 8 includes an inner core 210 from which a plurality of flutes 212 extend. In some embodiments, the inner core 210 has a tapered, conical or press fit geometry positioned and oriented for where it is most likely (at least in some cases) to encounter "harder" bone, and the flutes 212 are positioned where they are most likely to encounter "softer" bone. In some embodiments the general shape of the modular stem 200 facilitates implantation in a relatively close orientation and position to a pre-defined orientation and position.

Figure 6:
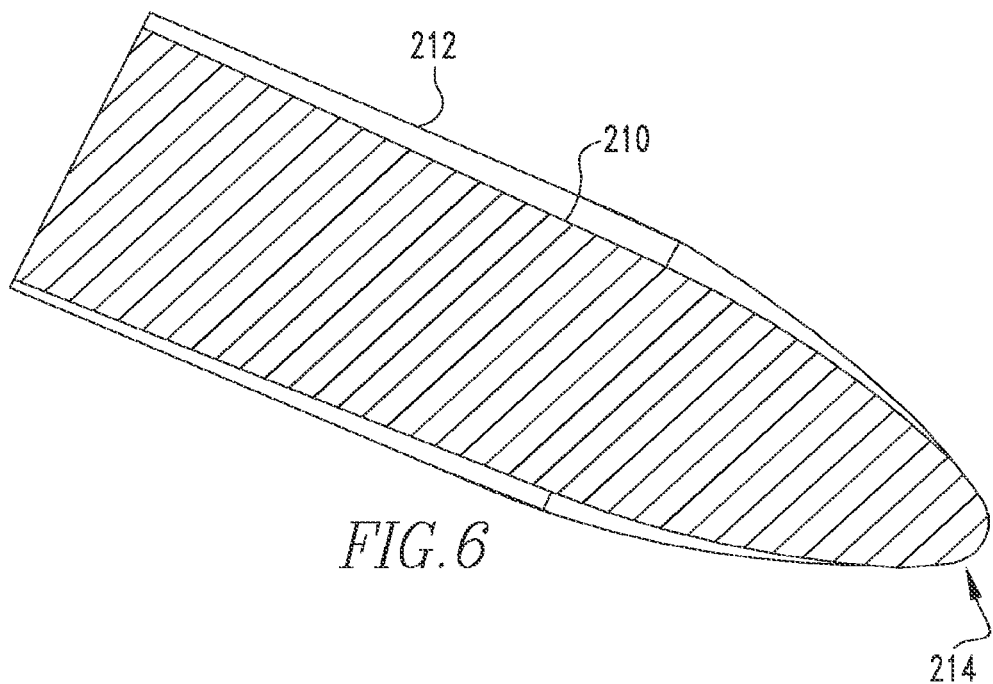
FIG. 6 is a cross-section of the stem of FIG. 4 taken along line 6-6 shown in FIG. 5.

As shown in FIG. 6, the inner core 210, in some embodiments, may be slightly tapered and/or define a somewhat conical shape. Conical features such as this one (whose axes, at least in some embodiments, may be directed generally parallel to the direction of load application) may be beneficial because, in some uses, they may convert what otherwise would be a purely compressive load into a compressive load that also has a transverse component (i.e. a direction of which could be characterized, at least in some embodiments, as orthogonal to the direction of the compressive load). In some embodiments, this may be beneficial in preventing bone immediately adjacent to the implant from being shielded from loading, at least for some of the time. In some cases, bone that is shielded from loading could remodel, resorb or otherwise degrade, resulting in a poor quality bone-implant interface. The tapered or conical shape of the modular stem 200 may also facilitate the prevention of subsidence or migration. The tapered or conical nature of the inner core 210 may also facilitate a press-fit type interface between the implant and bone. In the embodiment shown, a distal tip 214 of the inner core is rounded.

Figure 4:
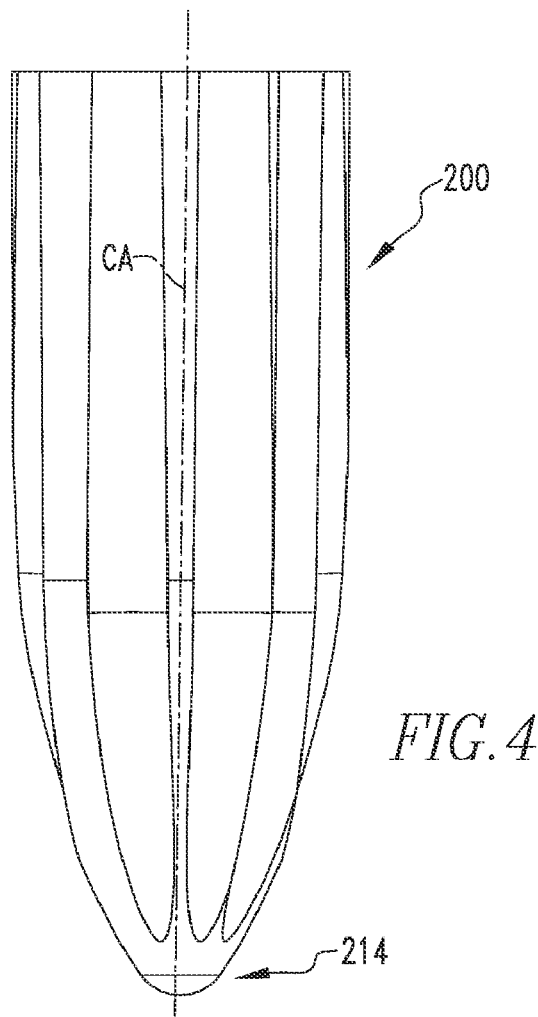
FIG. 4 illustrates a modular stem that may optionally be used with the tibial tray of FIG. 1.
Figure 5:
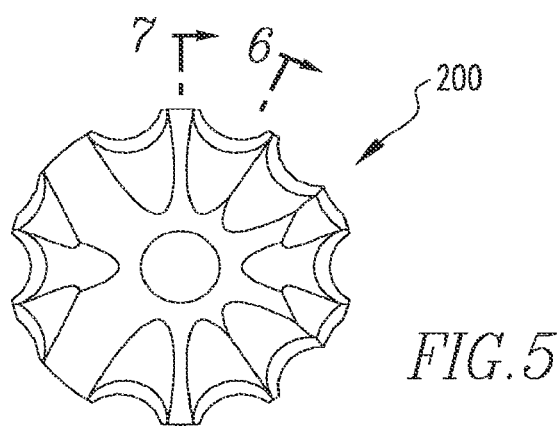
FIG. 5 is a distal view of the modular stem of FIG. 4.
Figure 7:
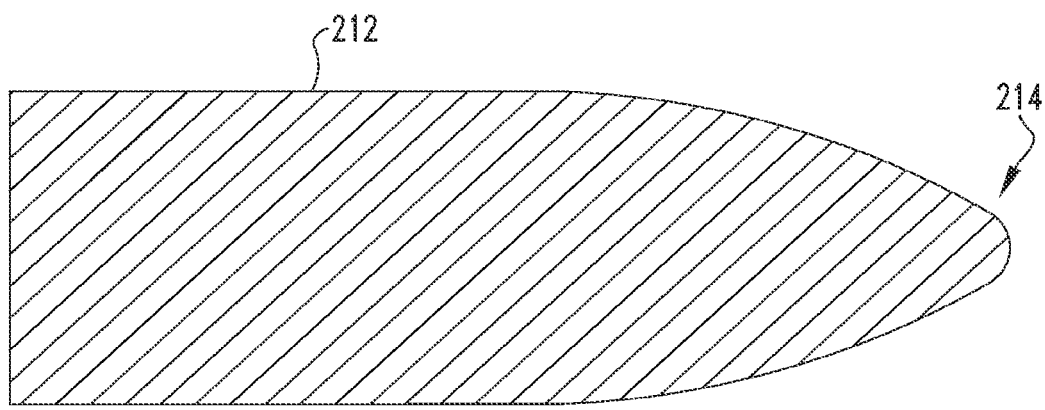
FIG. 7 is a cross-section of the stem of FIG. 4 taken along line 7-7 shown in FIG. 5.

As shown in FIGS. 4, 5, and 7, several flutes 212 extend radially from the inner core 210 of the modular stem 200. In the particular embodiment shown, the flutes 212 extend in a radially symmetric pattern such that the apexes of the flutes 212 are parallel to a central axis CA of the inner core 210. In other words, although the inner core tapers, the apexes of the flutes extend along a virtual cylinder. In other embodiments, the apexes of the flutes may also taper as they extend towards the distal tip of the stem; although, in at least some of these embodiments, the flutes do not taper as much as the inner core. Because, at least in some embodiments, the inner core tapers to a greater degree than the apex of the flutes, the flutes will "protrude" from the stem to a greater extent at distal portions of the stem than at proximal portions of the stem. Accordingly, in some embodiments, such a design may pose less of a risk of fracturing the hard bone that is located proximate the proximal portions of the stem while still achieving fixation (rotational and/or translational) in the soft bone located proximate the distal portions of the stem. Additionally, in some embodiments, there may be less of a risk of deflection or mal-orientation or mal-position due to lack of or lessening of press-fit between the flutes and the hard bone.

Figure 8:
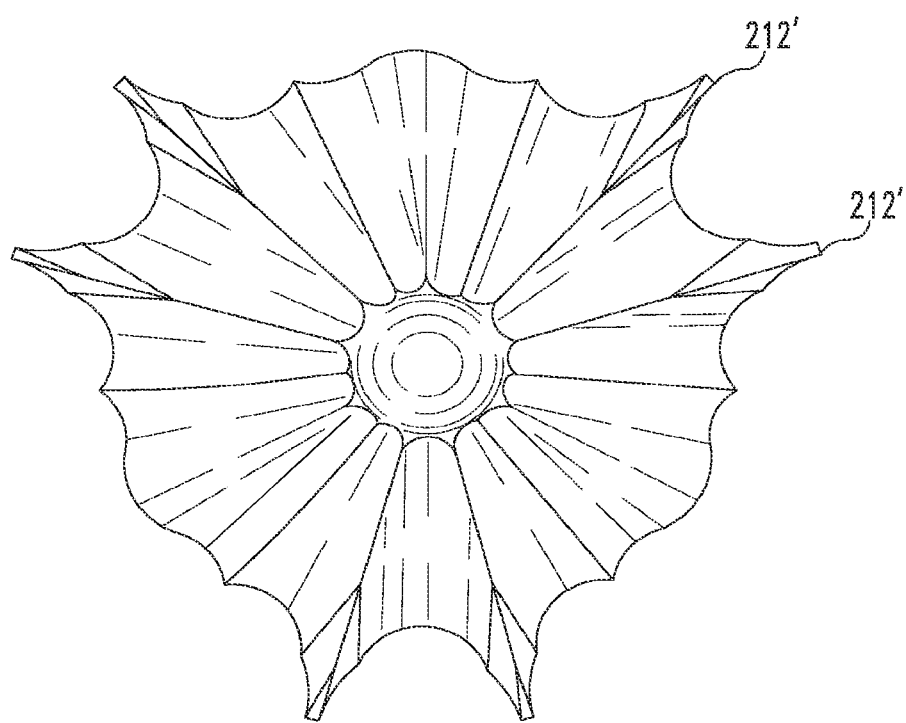
FIG. 8 illustrates a distal view of an alternative embodiment of fluting useable with a modular stem such as the modular stem of FIG. 4.

As shown best in FIG. 8, in addition to the flutes 212 described in the previous paragraph, the inner core of the modular stem may also include secondary/smaller fluting 212' extending therefrom. In some embodiments, the secondary fluting 212' may be rounded or sharp, and may further facilitate a tight fit with the surrounding bone, while, because they are smaller, lessening the chance of tibial pain. In some embodiments, the fluting is radially symmetric and facilitates insertion of the stem 200 to follow a pilot hole. FIG. 8 shows fluting useable in some embodiments of modular stems in which the stem 200 has fluting (or at least primary fluting) that is spaced 120 degrees apart.

In some embodiments, the fluting is not radially symmetrical, but instead exhibits planar symmetry. Planar symmetry may allow, in some embodiments, matching of the fluting to the support member geometry of a tibial component. In some embodiments, the fluting is not radically symmetrical and is instead "handed" and specific for left or right tibias to accommodate particular or expected locations of hard and soft bone. In some embodiments, patient matched technologies could be employed to customize the fluting to the hard vs. soft bone distribution of the specific patient.

In some embodiments, the fluting may be tapered. In some embodiments, the "soft bone flutes" may be designed in such a way that over small sections, they may be lower than the "hard" bone flutes. In some embodiments, the "soft" bone flutes could be parallel to the "hard" bone flutes but become tangentially wider to increase their effectiveness in soft bone. In some embodiments, the flutes could be discontinuous. In some embodiments, the flutes could be made of a material different than that of the rest of the stem. In some embodiments, portions of the stem could be porous coated or have surface finishes applied.

Figure 9:
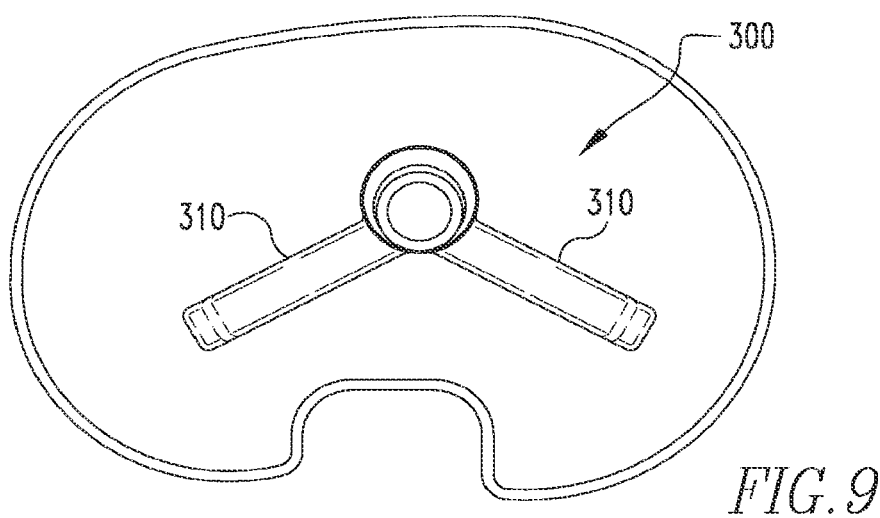
FIGS. 9-14 illustrate schematically an alternative embodiment of a tibial tray with a modular stem.
Figure 10:
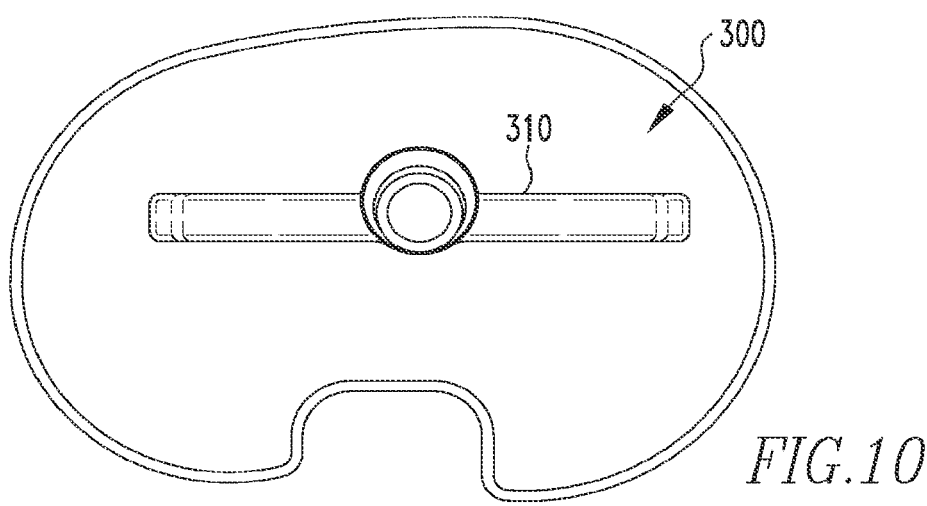
Figure 11:
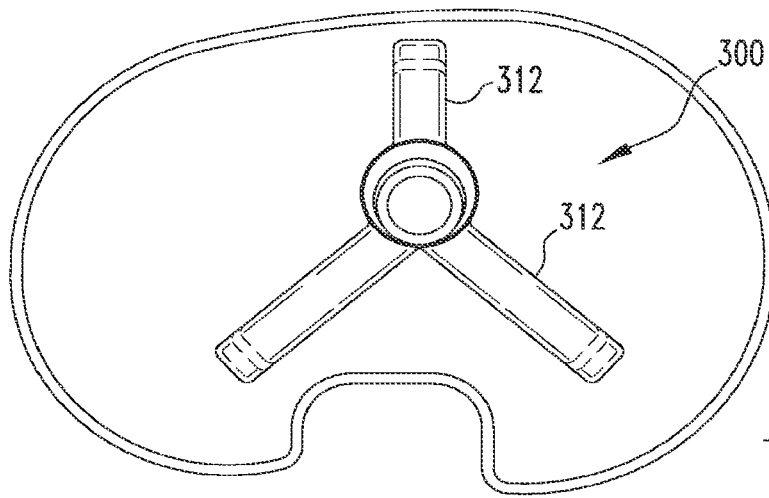
Figure 12:
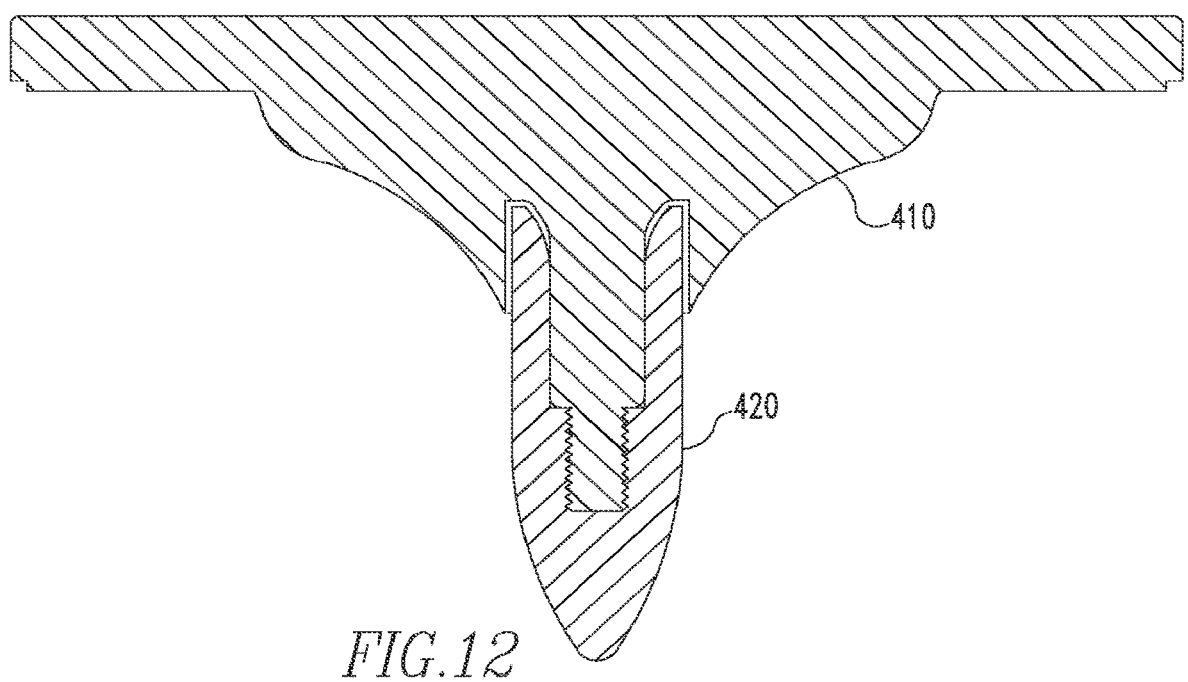

FIGS. 9-11 illustrate alternative possible support member shapes. For example, in FIGS. 9 and 10, there are two branches 310 (or arms or wings) of the support member 300. In FIG. 9, the branches 310 are angled relative to one another, but in FIG. 10 the branches 310 are substantially aligned with one another. In FIGS. 11 and 12, the support member 300 has three branches or arms 312. Fewer or greater numbers of branches are possible.

Figure 13:
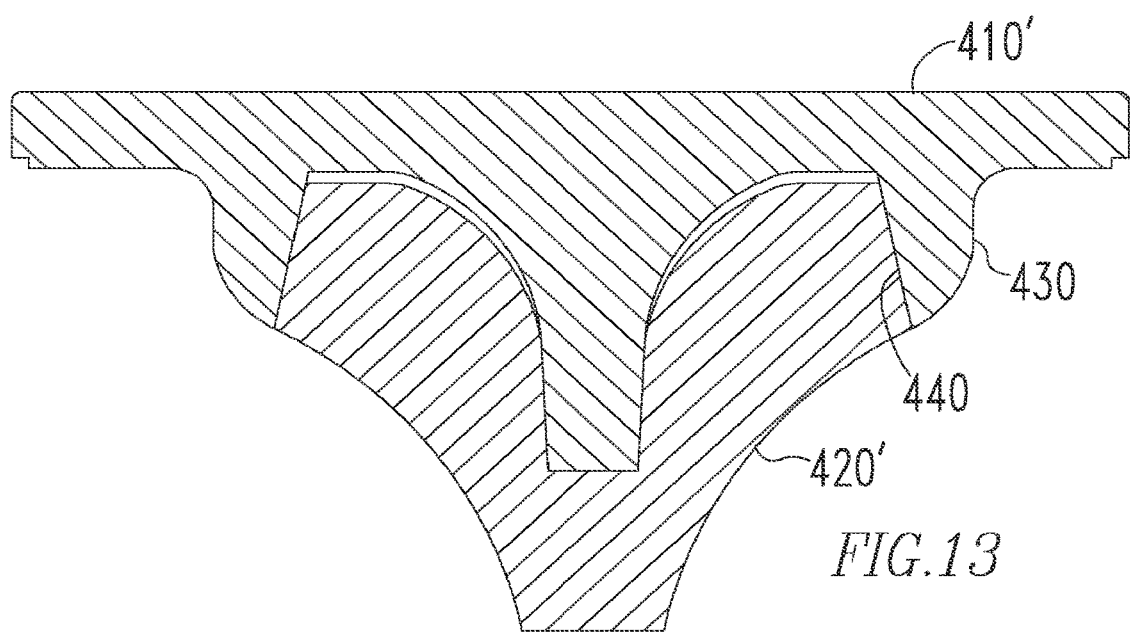
Figure 14:
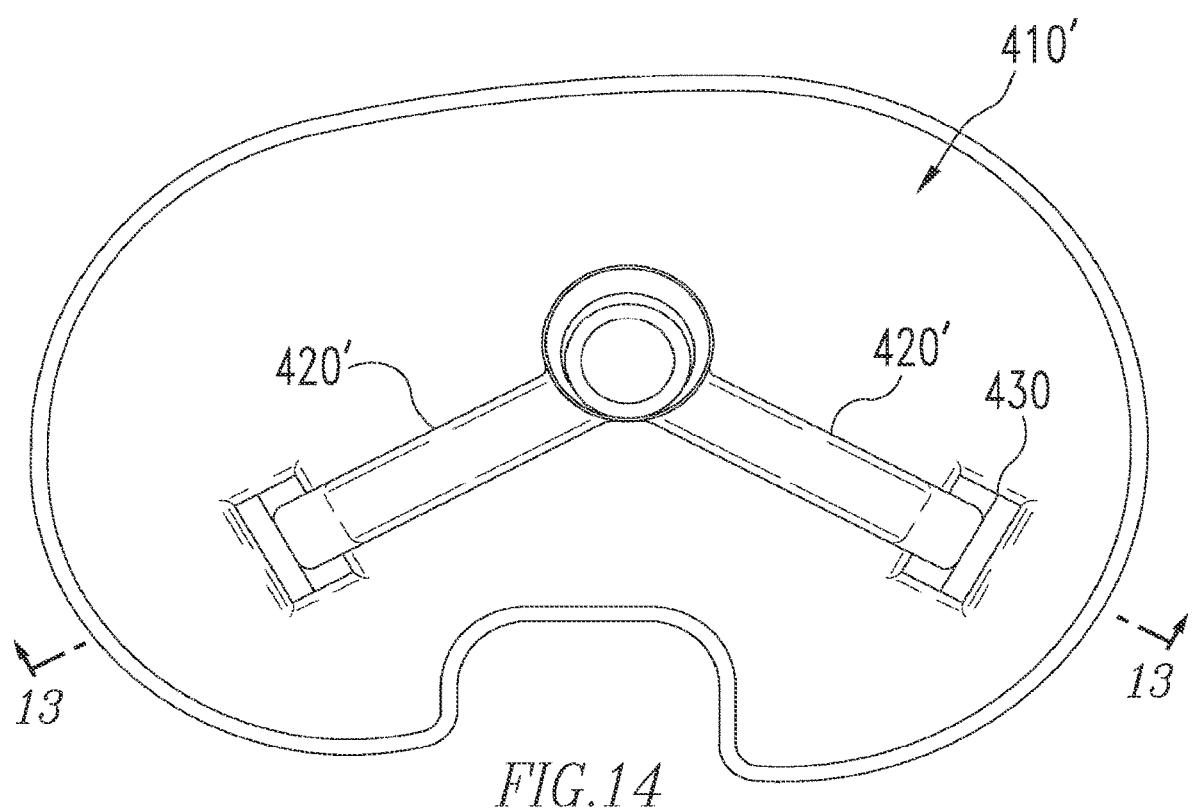
Figure 19:
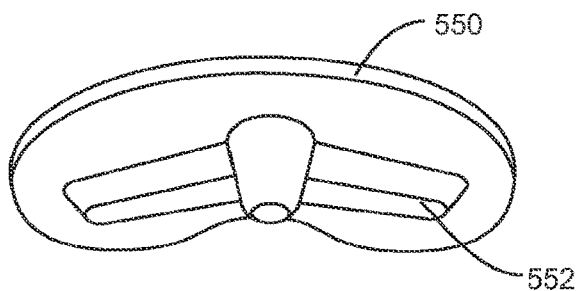
FIGS. 19-22 illustrate tibial trays having a fin.

As illustrated in FIGS. 12, 13 and 14, the tibial tray 410 and support member 420 may be modular and may have a male/female arrangement. Although in the Figures the stem portion 420 is shown to have a female portion and the tibial tray 410 is shown to have a male portion, these could be reversed. In the embodiment depicted in FIG. 13, the tibial tray 410' has a shoulder 430 that engages a ledge 440 of the stem portion 420'. The shoulder/ledge arrangement allows force to be transferred from the tibial tray 410' to the stem portion 420'. The shoulder 430 also may provide a porous surface area for bone in-growth. As best seen in FIG. 13, the stem portion 420' may engage in a taper lock with a portion of the tibial tray 410'.

FIGS. 15-18 illustrate a finned platform 500 for mounting a cutting block 502. FIG. 15 illustrates a state of the art cutting block 502 having a spike 504 that is used to hold the block temporarily in place. The spike has certain drawbacks. For example, the cutting block may shift with an applied load as a surgeon tries to keep even contact between a sawblade 506 and the cutting surface 508. This may result in uneven or mal-rotated, poorly positioned cuts.

FIG. 16 illustrates a finned platform 500. The finned platform 500 has a head 510, a shaft 512, and fins 514 on the shaft 512. The head 510 has a planar surface at its uppermost portion or may have an enlarged planar surface 526 at its uppermost portion. The finned platform 500 may be cannulated as shown at 516 to receive a spike 518 of a bone cutting block 520 as shown in FIG. 18. The fins may be in the form of a thread 514' (finned platform 500' in FIG. 16b) or a plurality of ribs. The fins 514 may have a large surface to adequately engage soft, spongy bone. The fins and/or head may resist movement. The finned platform 500 may be made of metal or a polymer. In some embodiments, the finned platform 500 is removed after cutting the bone. In some embodiments, the finned platform 500 is left in after surgery to assist in mounting an implant to the bone. In some embodiments, the finned platform 500 is made from a resorbable material. In some embodiments, the finned platform 500 is made from a shape memory material. In use, the finned platform 500 is placed into bone 522. Optionally, a pilot hole 524 may be drilled prior to placement of the finned platform 500. A cutting block 520 with a spike 518 is engaged with the finned platform 500. In some embodiments, the spike may extend beyond the finned platform or vice versa. Thereafter, the cutting block 520 is used as guide by a sawblade 506, cutting tool, or other instrument. The finned platform 500 may stabilize the cutting block for more reproducible cuts. The finned platform 500 of the present invention may be used on either the femoral bone component or the tibial bone component to properly prepare the respective bone portion for receiving either a femoral knee implant or a tibial tray implant. FIG. 16*a* shows an alternative embodiment of the finned platform 530. The finned platform 530 is shown having a head 532, a shaft 534 and a plurality of fins 536 extending longitudinally along the shaft 534. There may be any number of fins 536, however, FIG. 16*a* shows the finned platform 530 having four equally spaced fins 536. The finned platform 530 may also be cannulated as shown at 538 to receive the spike 518 of a bone cutting block 520 (shown in FIG. 18). The benefit of the fins 514 and 536 of platforms 500 and 530 are to resist lateral movement of the cutting block as shown by arrows in FIG. 15 depicting the prior art.

Figure 20:
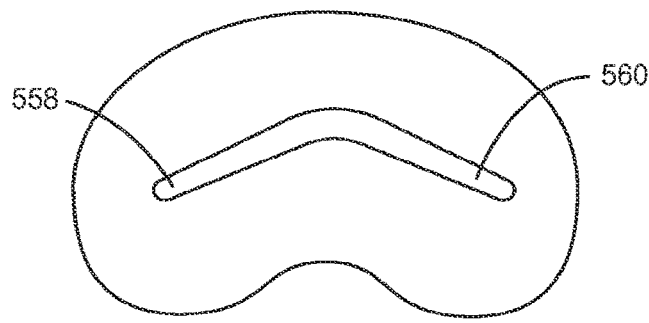
Figure 21:
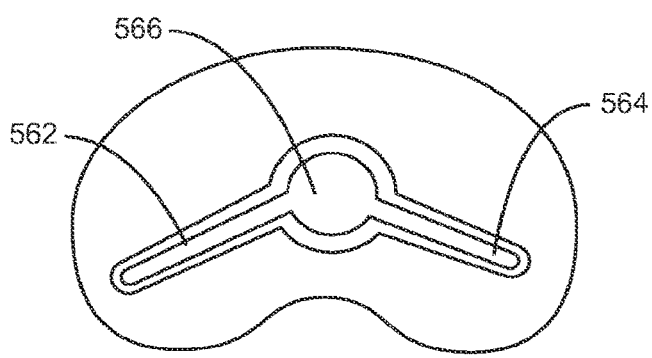
Figure 22:
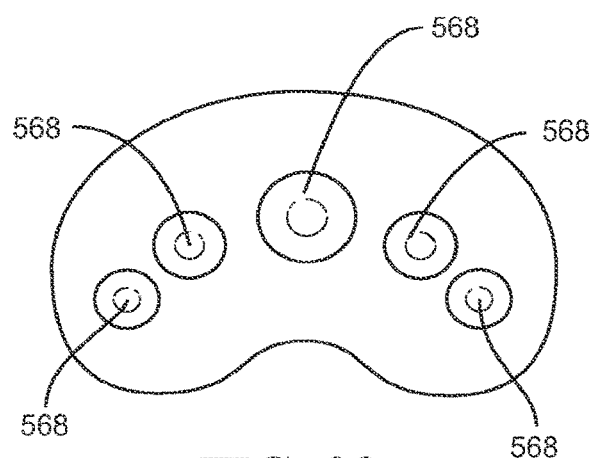

FIGS. 19-22 illustrate a tibial trial 550 having a fin 552. The fin 552 may be in the form of a raised portion 554 on the underside of the tibial trial 550. The top side of the tibial trial or implant is often called a tray 556. The tibial trial 550 with the fin 552 may be used to reinforce bone to reduce the risk of fracture during bone preparation. The tibial trial 550 with the fin 552 may aid in securing the tray 556 during trialing. During trialing, a number of trial inserts (not shown) may be positioned on the tray 556 to determine the correct spacing of the tibial implant with respect to the femoral implant portion of the overall knee implant. The tibial trial 550 with the fin 552 may aid in securing the tray 556 during bone preparation. The tibial trial 550 with the fin 552 may provide a foundation for other instruments, such as punches, reamers, and drills (not shown). As best seen in FIG. 20, the fin 552 may be in the form of two arms 558 and 560. And, as best seen in FIG. 21, the fin 552 may be in the form of two arms 562 and 564 with a center portion 566. As examples, the center portion 566 may be in the form of a circle, cylinder, square, rectangle, or triangle. As best seen in FIG. 22, the fin 552 may be in the form of a series of protrusions 568. For example, the fin 552 may be in the form of a series of cylinders. In use, the tibial trial 550 is placed upon bone and impacted to force the fin 552 into the bone. It would also be possible that the tibial trial has a plurality of holes placed where the protrusions 568 are shown to allow the user to drill a plurality of holes through the trial 550 and into the bone underneath the trial. It would then be easier to place the tibial tray implant into the bone without fracturing the bone site.

Figure 23:
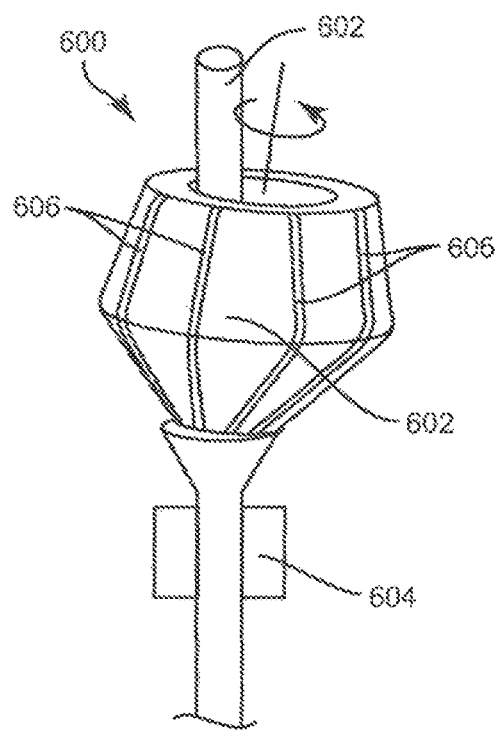
FIGS. 23-25 illustrate a rotatable reamer.
Figure 24:
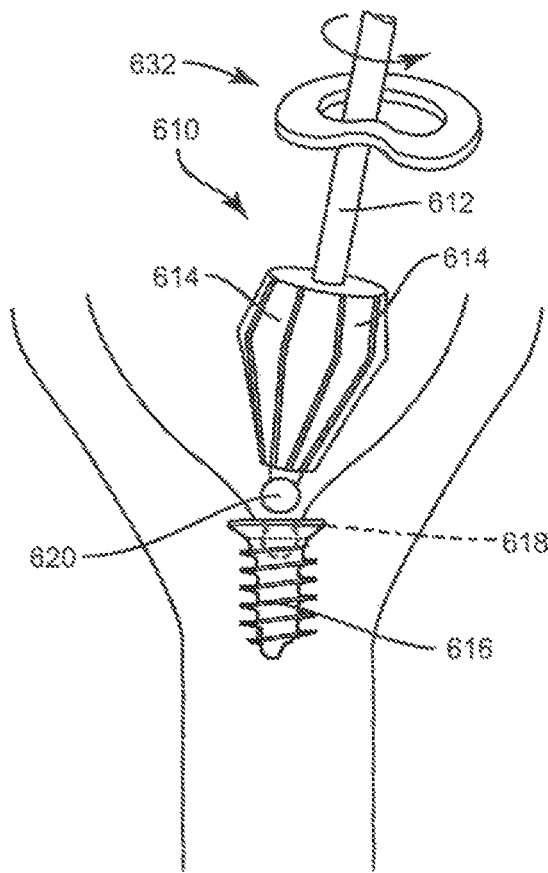
Figure 25:
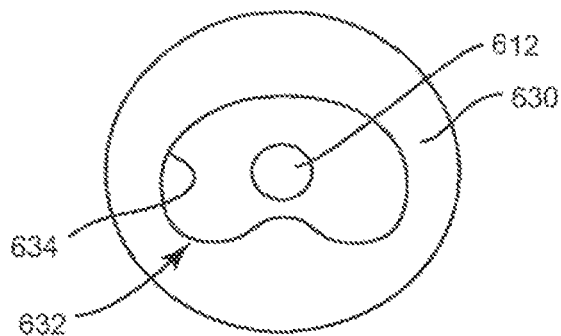

FIGS. 23-25 illustrate a reamer 600. FIG. 23 illustrates a reamer 600 in a first embodiment. The reamer 600 has a shaft 602, a depth stop 604 and one or more cutting flutes 606 mounted to the shaft 602. The shaft can be rotated and pivoted to engage the cutting flutes 606 with bone. The shaft 602 may have different shapes. In one embodiment, the shaft 602 may be circular, however the shaft 602 may also be oval (as shown in FIG. 23) or otherwise have any other more complex shape. The benefit of such a reamer is the ability to cut or carve out a non-circular portion of the bone. FIG. 24 illustrates a reamer 620 in a second embodiment. The reamer 610 has a shaft 612 and one or more cutting flutes 614 mounted to the shaft 612. The reamer 610 can be used in conjunction with an anchor 616. The anchor 616 would be inserted within a tibia, for example, to allow for the user to cut or carve out a portion of the bone. The anchor 616 may have a depression 618 to receive a tip 620 of the shaft 612 of the reamer 610. The tip 620 may be rounded. The anchor 616 may be temporary or permanently positioned within the tibia. The shaft can be rotated and pivoted to engage the cutting flutes 614 with bone. FIGS. 24 and 25 illustrate a guide 630 that can be used with the second embodiment of the reamer 610. The guide 630 has a stator 632 with a cam opening 634. The shaft 612 is moved along the cam opening 634 to restrict and or limit movement of the reamer within the bone. The shape of the cam opening 634 would determine the shape of the bone cutout in the tibia.

Figure 26:
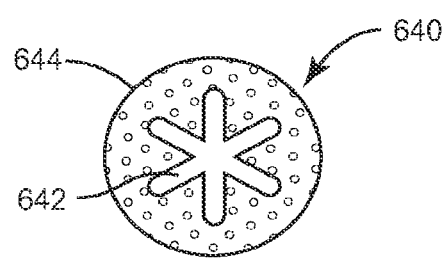
FIGS. 26-29 illustrate fixation pegs.
Figure 27:
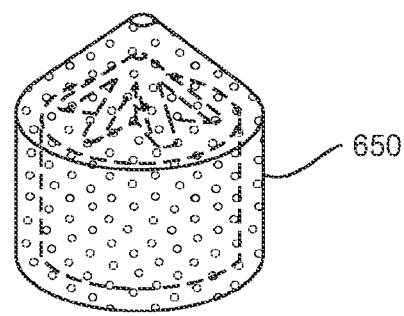
Figure 28:
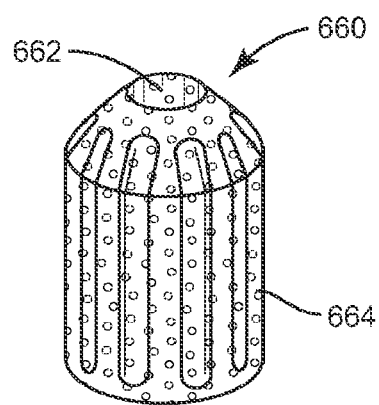
Figure 29:
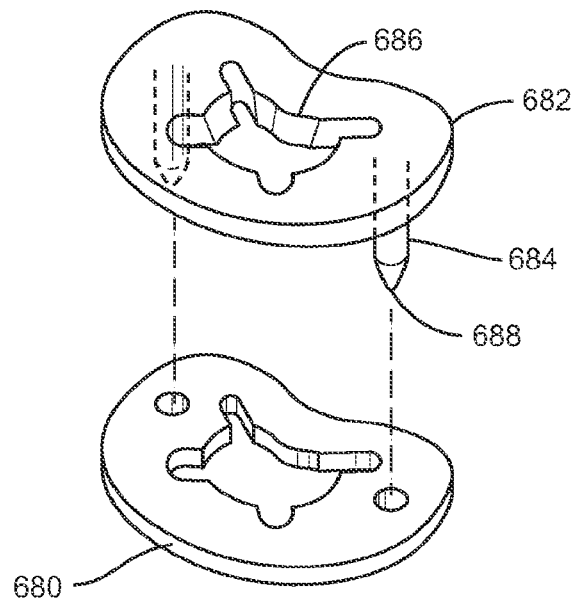

FIGS. 26-29 illustrate fixation pegs 640. The fixation pegs 640 are placed on both the tibial and femoral implant components to prevent such components from twisting once placed over the bone portion. FIG. 26 illustrates a fixation peg 640 with a solid center 642 and a porous outer portion 644. The shape of the solid center portion 642 provides a fixation peg 640 having portions that are thin enough such that a saw can cut through them but are still thick enough to withstand loading. This is significant as prior fixation pegs were such that a saw could not cut through without significant difficulty. Thus, the pegs shown in FIG. 26 may be beneficial if the implant must be replaced or revised. FIG. 27 illustrates a cap 650 (porous or solid) that can be placed over an existing solid fixation peg. FIG. 28 illustrates a peg 660 with a cylindrical solid core 662 and a porous exterior portion 664. The solid core 662 can be molded together with the porous exterior portion 664 or the porous exterior portion 664 can be slid over the solid core 662 during use. FIG. 29 illustrates a modular trial 680 and punch 682. The punch 682 can be attached to the trial 680 with a quick connect feature. The punch 682 may include a portion 684 to prepare for the lugs and a portion 686 to prepare for one or more arms (or fins). The portion 684 of the punch 682 may be in the form of spikes 688 which would pass through the trial 680 and into the bone underneath the trial. The pegs (like those shown in FIG. 26) of a tibial tray implant would then be inserted into the prepared holes in the bone.

Figure 30:
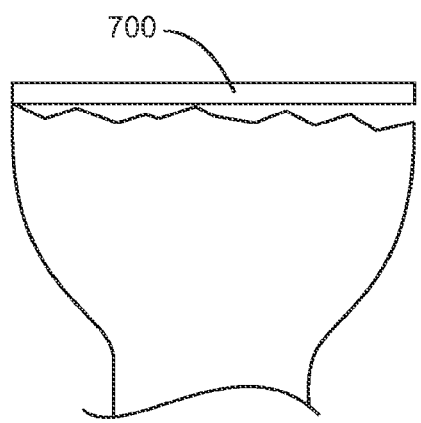
FIGS. 30-34 illustrate instruments for tibial surface preparation.
Figure 31:
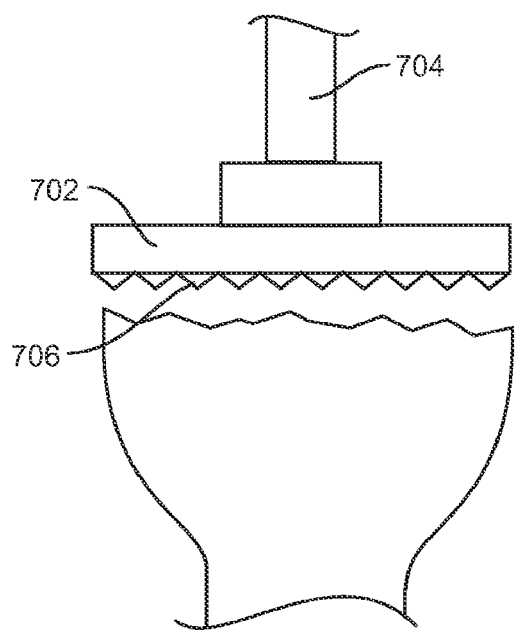
Figure 32:
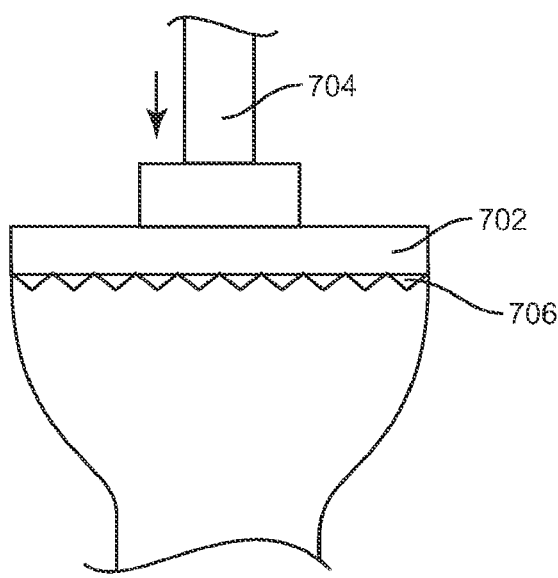
Figure 33:
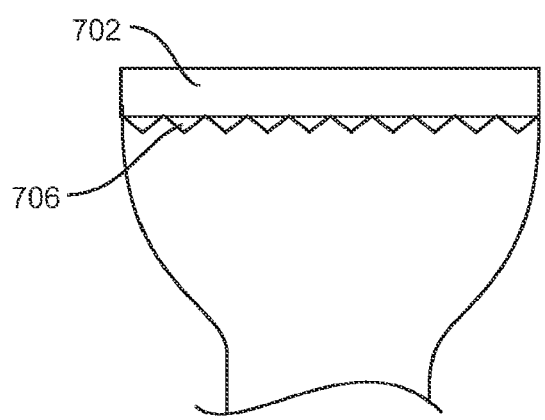
Figure 34:
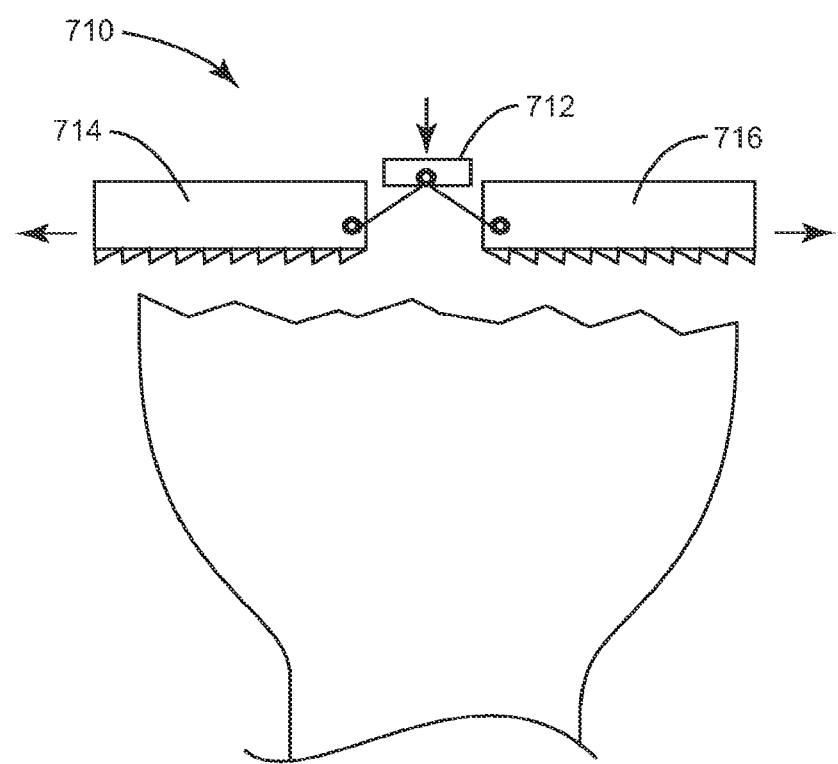

FIGS. 30-34 illustrate instruments for tibial surface preparation. FIG. 30 illustrates the current state of the art wherein there remains an uneven surface after the bone surface is cut. As shown therein a trial 700 could sit unevenly on top of an improperly cut tibial bone. FIGS. 31-33 illustrate a rasp 702 that is impacted on top of the tibial bone will produce a surface that is more planar. The rasp 702 may be struck by an impactor 704 one time or repeatedly until the rasp 702 is embedded onto the tibial bone to create an even uniform bone surface as shown in FIG. 33. In some cases, the bone will flow onto the teeth 706 of the rasp 702 to assist in creating an even bone surface. In some embodiments, the rasp may form a portion of or replace the trial. FIG. 34 illustrates a multi-part rasp 710. The rasp 720 has a center portion 712 that is struck by an impactor in the direction of the arrow. Impacting the center portion 712 forces the outer rasp portions 714 and 716 apart to cut and smooth the bone.

Figure 35:
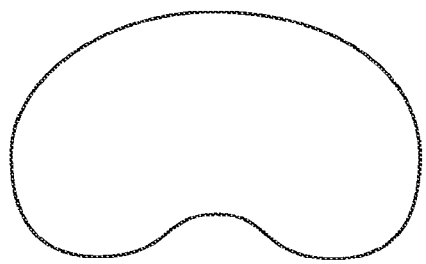
FIGS. 35-39 illustrate a tibial trial for tibial surface preparation.
Figure 36:
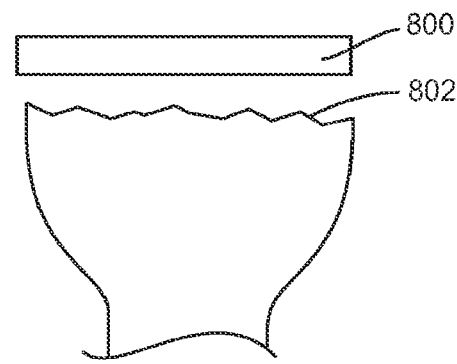
Figure 37:
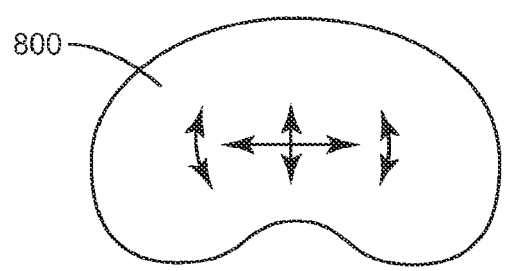
Figure 38:
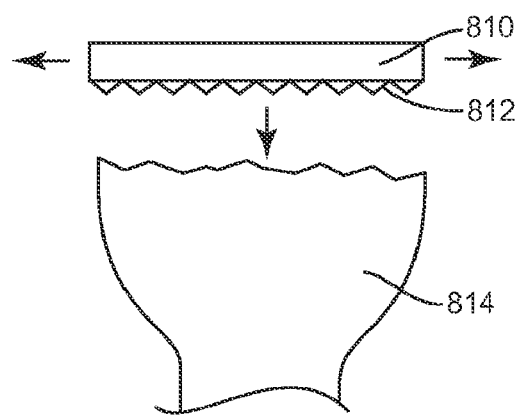
Figure 39:
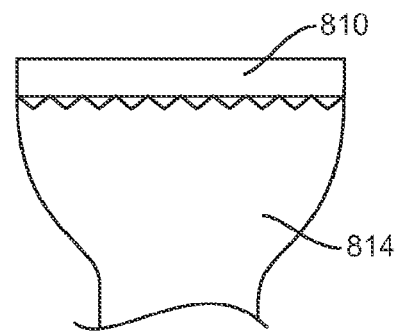

FIGS. 35-39 illustrate a tibial trial 800 for tibial surface preparation. FIGS. 35 and 36 illustrate the state of the art. The tibial trial 800 is placed upon the prepared surface after cutting of the tibial bone. However, the prepared surface is shown uneven such that the trial 800 does not sit well upon the prepared surface 802. FIGS. 37-39 illustrate a trial 810 with a build-in rasp 812. In use, the bone 814 is cut and the surface is prepared. The combination trial 810 and rasp 812 is placed upon the bone surface and moved in the directions of the arrows shown in FIG. 37 to engage the rasp 812 with bone. For example, the combination trial 810 and rasp 812 may be rotated or moved in an A-P or M-L direction to engage the rasp 812 with bone 814 to cut and smooth the surface. Thereafter, normal trialing may be carried out and an implant can be properly mounted to the bone.

One of skill in the art will recognize that changes, deletions, alterations, additions and other modifications could be made to the non-limiting embodiments described above without departing from the scope or spirit of the inventions described herein.

I claim:

1. A method of preparing a patient's tibia comprising:
    positioning a bone anchor into the patient's tibia, wherein the bone anchor comprises: a head having an upper support surface including a depression, a shaft depending from the head, the shaft insertable within the patient's tibia, and a fin laterally extending from the shaft for engaging the patient's tibia upon insertion of the shaft and the fin into the patient's tibia;
    positioning a cutting instrument into contact with the bone anchor, wherein the cutting instrument comprises: a shaft portion including one or more cutting elements and a rounded tip portion receivable within the depression formed in the head of the bone anchor to removably couple the cutting instrument with the bone anchor so that the cutting instrument can rotatably and pivotally move relative to the bone anchor to enable the one or more cutting elements to cut the patient's tibia; and
    rotating the cutting instrument relative to the bone anchor to cut portions of the patient's tibia.

2. The method of claim 1, wherein cutting portions of the patient's tibia comprises carving out portions of an interior portion of the patient's tibia.

3. The method of claim 1, wherein positioning a bone anchor into the patient's tibia comprises inserting the bone anchor into the intramedullary canal of the patient's tibia.

4. The method of claim 1, further comprising removing the bone anchor from the patient's tibia.

5. The method of claim 1, wherein the bone anchor comprises a bone screw.

6. The method of claim 1, wherein the upper support surface of the head of the bone anchor includes a planar surface.

7. The method of claim 1, wherein the fin is a continuous thread extending about the shaft.

8. The method of claim 1, wherein the fin includes a plurality of ribs extending about the shaft.

9. The method of claim 1, wherein the fin includes a plurality of longitudinally extending ribs extending along the shaft.

10. The method of claim 1, further comprising guiding movement of the cutting instrument within the patient's tibia.

11. The method of claim 10, wherein guiding movement of the cutting instrument within the patient's tibia comprises:
    providing a guide arranged and configured to interact with the shaft portion of the cutting instrument to guide movement of the cutting instrument within the patient's tibia.

12. The method of claim 11, wherein the guide includes a stator with a cam opening, the shaft portion of the cutting instrument is positioned within the cam opening and is moved along the cam opening to guide movement of the cutting instrument.

13. The method of claim 1, wherein the cutting instrument comprises a reamer.

14. The method of claim 1, wherein the one or more cutting elements comprise one or more cutting flutes that do not extend across the tip portion.

15. A method of preparing a patient's proximal portion of a tibia adjacent a knee joint, the method comprising:
    threadably inserting a bone anchor into an intramedullary canal of the patient's tibia, the bone anchor including a head having an upper support surface including a depression;
    positioning a cutting instrument into contact with the bone anchor, the cutting instrument including a shaft portion including one or more cutting elements and a tip portion receivable within the depression formed in the head of the bone anchor to removably couple the cutting instrument with the bone anchor; and
    rotatably moving the cutting instrument relative to the bone anchor to enable the one or more cutting elements to engage with the patient's tibia.

16. The method of claim 15, further comprising guiding movement of the cutting instrument within the patient's tibia, wherein guiding movement of the cutting instrument comprises:
    providing a guide including a cam opening; and
    positioning the shaft portion of the cutting instrument through the cam opening; and
    moving the shaft portion along the cam opening to guide movement of the cutting instrument.

* * * * *